(12) United States Patent
Singh et al.

(10) Patent No.: US 8,771,471 B2
(45) Date of Patent: *Jul. 8, 2014

(54) PROCESS FOR MAKING ABSORBENT COMPONENT

(71) Applicant: The Procter & Gamble Company, Cincinnati, OH (US)

(72) Inventors: Anirudh Singh, Cincinnati, OH (US); Christopher Michael Young, Loveland, OH (US); Timothy Duane Smith, Cincinnati, OH (US); Steven Lee Barnholtz, West Chester, OH (US); Dirk Saevecke, Wiesbaden (DE); Gina Isoldi, Brussels (BE); Florian Philip Rousselange, Neu-Isenburg (DE); Norbert Matthias Stelzer, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/748,637

(22) Filed: Jan. 24, 2013

(65) Prior Publication Data

US 2013/0228948 A1 Sep. 5, 2013

Related U.S. Application Data

(60) Provisional application No. 61/606,533, filed on Mar. 5, 2012.

(51) Int. Cl.
*D21F 13/00* (2006.01)

(52) U.S. Cl.
USPC .......................................................... 162/218

(58) Field of Classification Search
USPC ............. 162/218, 20, 281, 55; 241/28, 27, 3, 241/222, 277; 100/41
See application file for complete search history.

(56) References Cited

U.S. PATENT DOCUMENTS

| | | |
|---|---|---|
| 3,994,771 A | 11/1976 | Morgan et al. |
| 4,241,881 A | 12/1980 | Laumer |
| 4,300,981 A | 11/1981 | Carstens |
| 4,650,127 A | 3/1987 | Radwanski et al. |
| 2004/0129392 A1 | 7/2004 | Crane et al. |
| 2013/0037635 A1* | 2/2013 | Singh et al. ................. 241/3 |

OTHER PUBLICATIONS

International Search Report, mailed May 3, 2013; 8 pages.

* cited by examiner

*Primary Examiner* — Mark Halpern
(74) *Attorney, Agent, or Firm* — Andrew J. Hagerty; Andrew J. Mueller

(57) ABSTRACT

A process for making an absorbent component comprising the steps of providing individual sheets of pulp; attaching a first individual pulp sheet to one or more second individual pulp sheets to form a strip of pulp; feeding the strip of pulp into a defiberizer; defiberizing the strip of pulp to form defiberized fibers; and depositing the defiberized fibers onto a forming surface to form the absorbent component.

20 Claims, 8 Drawing Sheets

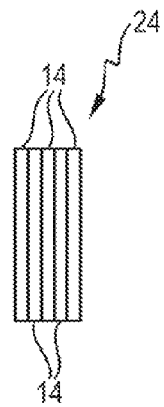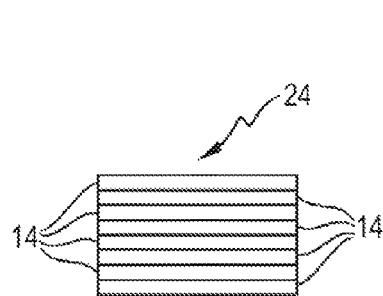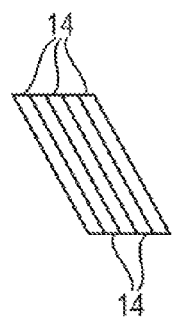
Fig. 2A   Fig. 2B   Fig. 2C
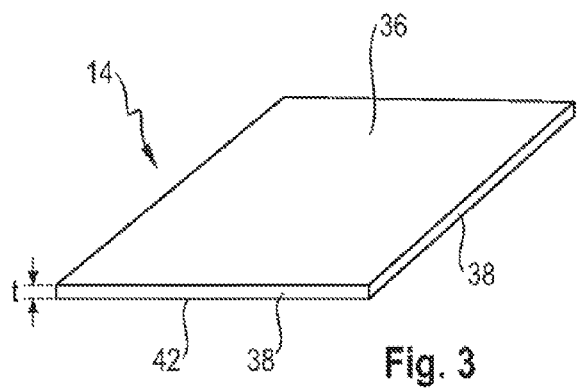
Fig. 3
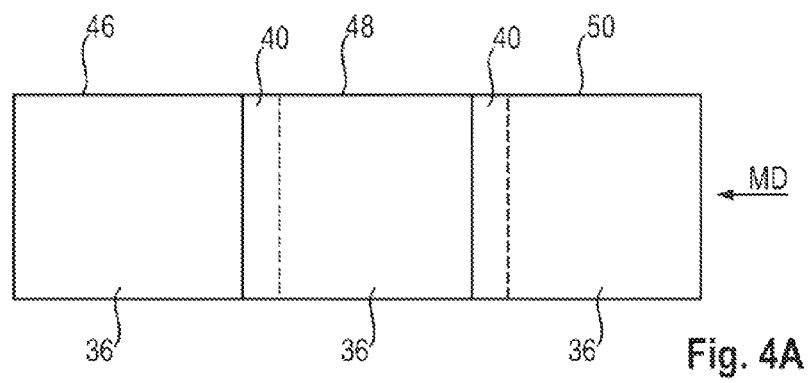
Fig. 4A

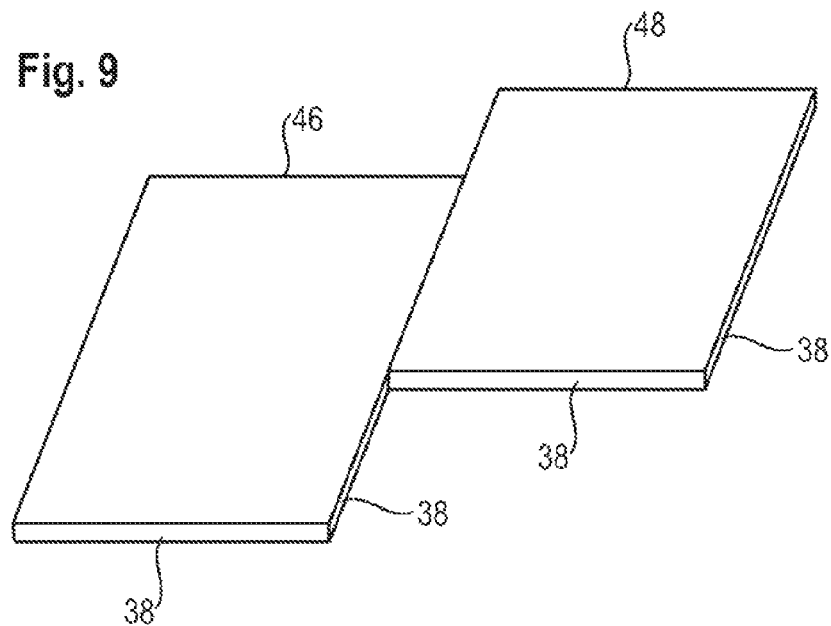
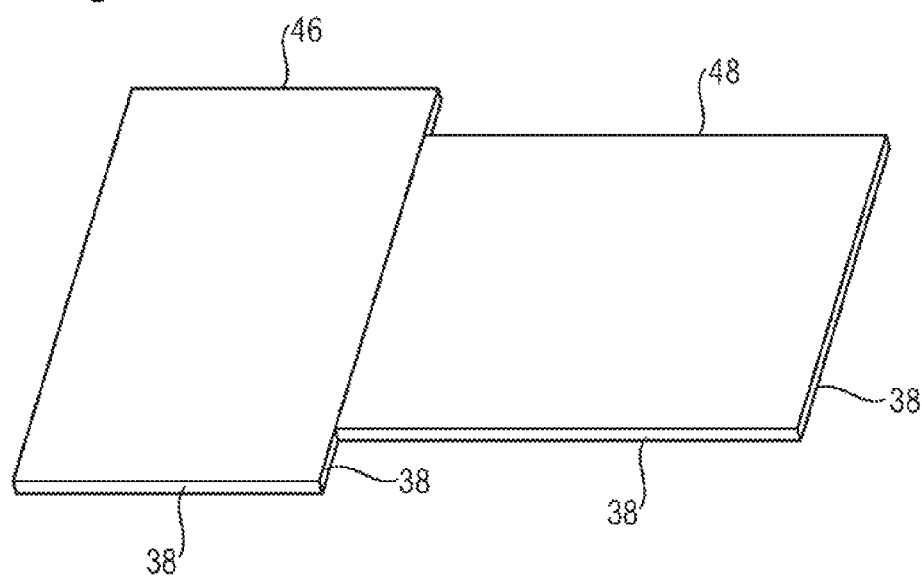

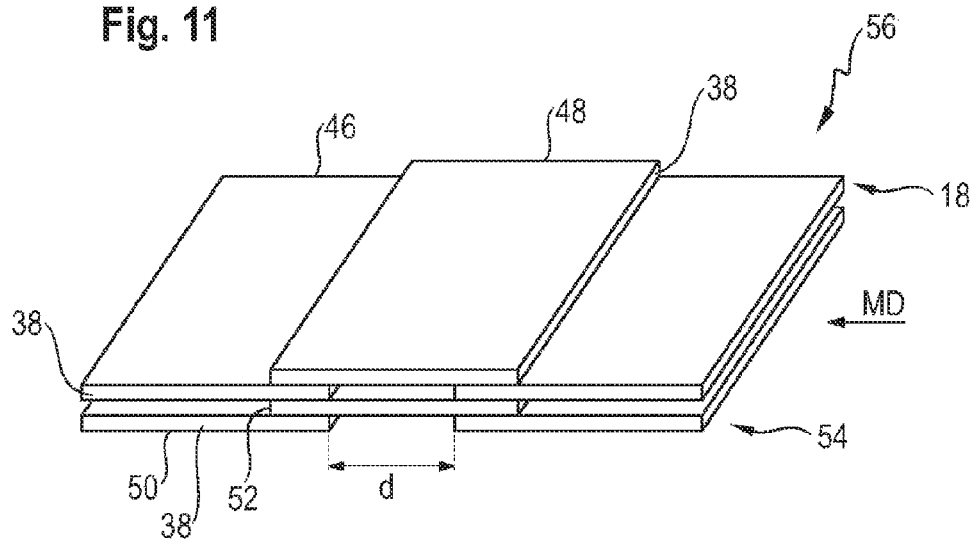
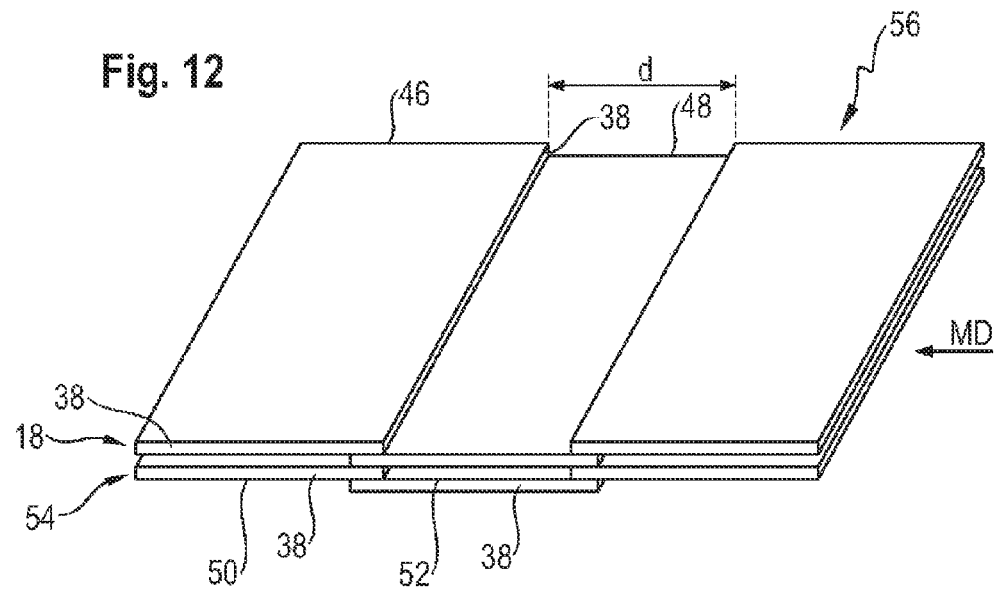

PROCESS FOR MAKING ABSORBENT COMPONENT

FIELD OF THE INVENTION

The present invention relates to a process for making an absorbent component from individual pulp sheets.

BACKGROUND OF THE INVENTION

Pulp fibers are used in the manufacture of many absorbent components for absorbent articles including, for example, diapers, feminine products, adult incontinence products, and paper products. The pulp fibers used to produce these products are supplied as rolled pulp or bale pulp. Rolled pulp is generally a continuous roll of a type of pulp known as fluff pulp. In comparison, bale pulp generally consists of a stack of individual pulp sheets. Two primary methods exist to process bale pulp and rolled pulp to obtain the individual fibers generally required to manufacture fibrous products. One method is an air-laid process where a defiberizer, such as a hammermill, interacts with the pulp to separate the individual fibers of the individual sheet or roll of pulp. The defiberizer exposes the fibers in the pulp while avoiding clumping and other adverse conditions that may cause apparent defects in an end product. The separate fibers are suspended in air and subsequently transferred to a forming surface such that an embryonic absorbent component is formed. The other method used to produce absorbent components is a wet-laid process. In a wet-laid process, pulp, typically in the form of individual sheets of pulp, is supplied to a device where the pulp is mixed with an aqueous solution to form a fibrous slurry. The fibrous slurry is then deposited onto a forming wire or belt such that an absorbent component is formed.

Sheet pulp or fluff pulp may be used in both an air-laid process and a wet-laid process. In air-laid processes, fluff pulp or rolled pulp has been the primary choice among manufacturers. Fluff pulp is the preferred material in air-laid processes because of its structural characteristics, such as a lower moisture content and more uniform density. In addition, fluff pulp is supplied in roll form allowing for a continuous strip of pulp to be fed into the defiberizer without creating any interruption in the defiberizing process. An interruption is characterized by a break or inconsistency in laying down fibers on a forming surface. Avoiding an interruption is important to the quality of products produced by the process. For the above reasons, manufacturers using an air-laid process generally choose rolled pulp to produce fibrous products.

Further to the above, manufactures have usually avoided using bale pulp in air-laid processes because of interruptions in the defiberizing process. When dealing with short, individual sheets of pulp, it is often the case that one sheet of pulp is pulled into the defiberizer at a faster rate than a subsequent sheet of pulp can be fed into the defiberizer. This gap in feeding sheets of pulp into the defiberizer can create an interruption in the supply of individual fibers to a forming surface. The resulting interruption in the defiberization process ultimately may result in an inconsistent, varied product. Such an interruption in the production of an absorbent component for an absorbent article could result in a product having inadequate absorbency or inferior softness.

Sheet pulp and rolled pulp are generally made of the same raw material. Despite this similarity, individual sheets of pulp offer some advantages over rolled pulp. Sheet pulp is less expensive than rolled pulp and can be transported and stored more easily than rolled pulp. The cost difference between rolled pulp and bale pulp is due in part to the process used to produce bale pulp, which is a less expensive process than that used to produce rolled pulp. In addition, bale pulp is produced by a large number of sources and, therefore, offers manufacturers more choice in suppliers and the ability to localize supply with the point of demand. In comparison, fluff pulp is a specialized grade of pulp that is produced by an expensive processes requiring large costly machinery. The expense of the equipment itself coupled with the expense to operate the equipment has resulted in relatively few suppliers of fluff pulp. As a result, fluff pulp represents a small percentage of the overall pulp market. Therefore, sheet pulp offers economic benefits over fluff pulp.

Due to the benefits of using bale pulp, processes for defiberizing individual sheets of pulp have been developed to try to combat the problem of fiber interruption. For example, defiberizers have been developed for accepting numerous unattached sheets of pulp that have been laid against of one another; that is numerous sheets of pulp in shingled relation enter the defiberizer at one time. Another apparatus has been developed to defiberize a pulp sheet with two defiberizing mechanisms in angled relation so that the force exerted on the pulp sheet is not parallel to the machine direction, and the feed of the pulp sheet can be controlled more easily. Still another apparatus that has been developed shreds the sheets of pulp and stores the shredded pulp in a hopper to create a uniform supply of shredded pulp for defiberization. Another method involves folding the sheets of pulp, where the fold line is parallel to the machine direction, to create a sheet of uniform thickness to be fed into the defiberizer. Generally, the above-discussed processes keep the sheets of pulp essentially separate from one another, which could still result in an interruption of fibers. In other words, the individual sheets of pulp in the existing processes are not attached to one another.

Accordingly, there is a need for a process that is capable of transforming individual sheets of pulp into a strip of pulp that simulates a continuous roll of pulp being fed into a defiberizer to form an absorbent component.

SUMMARY OF THE INVENTION

The present disclosure fulfills the need described above by providing a process for making an absorbent component, the process comprising the steps of providing individual sheets of pulp; attaching a first individual pulp sheet to one or more second individual pulp sheets to form a strip of pulp; feeding the strip of pulp into a defiberizer; defiberizing the strip of pulp to form defiberized fibers; and depositing the defiberized fibers onto a forming surface to form the absorbent component.

BRIEF DESCRIPTION OF THE DRAWINGS

FIG. 2A is a schematic, side view of an example embodiment of a stack of individual pulp sheets;

FIG. 2B is a schematic, side view of another example embodiment of a stack of individual pulp sheets;

FIG. 2C is a schematic, side view of another example embodiment of a stack of individual pulp sheets;

FIG. 3 is a schematic, perspective representation of an example embodiment of an individual pulp sheet;

FIG. 4A is a schematic, top view of an example embodiment of a strip of pulp;

FIG. 9 is a schematic, perspective representation of another example embodiment of a strip of pulp;

FIG. 10 is a schematic, perspective representation of another example embodiment of a strip of pulp;

FIG. 11 is a schematic, perspective representation of another example of a strip of pulp;

FIG. 12 is a schematic, perspective representation of another example of a strip of pulp;

DETAILED DESCRIPTION

Figure 1:
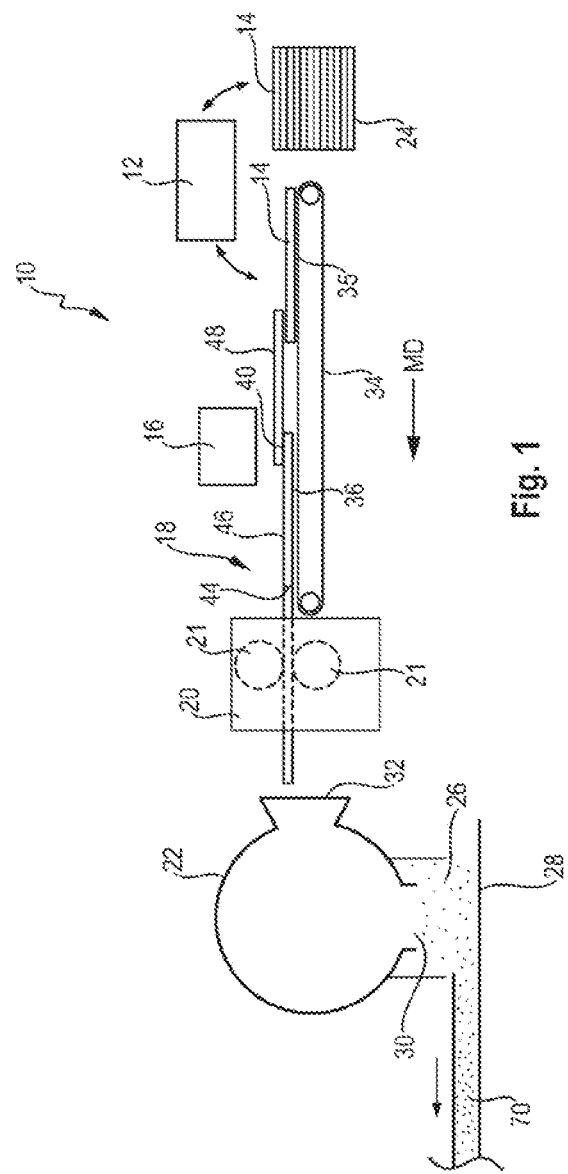
FIG. 1 is a schematic, side view of an example embodiment of a process of the present invention.

Various non-limiting embodiments of the present disclosure will now be described to provide an overall understanding of the principles of the process as disclosed herein. One or more examples of these embodiments are illustrated in the accompanying drawings. Those of ordinary skill in the art will understand that the process for making an absorbent component from individual sheets of pulp as described herein and the accompanying drawings are non-limiting embodiments and that the scope of the various embodiments of the present disclosure are defined solely by the claims. The features illustrated or described in connection with one embodiment can be combined with the features of other embodiments. Such modifications and variations are intended to be included within the scope of the present disclosure.

DEFINITIONS

Non-limiting examples of processes for making absorbent components include known wet-laid papermaking processes and air-laid papermaking processes. Such processes typically include steps of preparing a fiber composition in the form of a suspension in a medium, either wet, more specifically aqueous medium, or dry, more specifically gaseous, i.e. with air as a medium. The aqueous medium used for wet-laid processes is oftentimes referred to as a fiber slurry. The fibrous slurry is then used to deposit a plurality of fibers onto a forming wire or belt such that an embryonic absorbent component is formed, after which drying and/or bonding the fibers together results in a absorbent component. Further processing the absorbent component may be carried out such that a finished absorbent component is formed. For example, in typical processes, the finished absorbent component is the absorbent component that is wound on a reel at the end of the process, and may subsequently be converted into a finished product, e.g. an absorbent article.

"Fiber" as used herein means an elongate particle having an apparent length greatly exceeding its apparent width, i.e. a length to diameter ratio of at least about 10. A "fiber" is an elongate particle as described above that exhibits a length of less than 5.08 cm (2 in.). Fibers are typically considered discontinuous in nature. Non-limiting examples of fibers include natural fibers including cotton, wood pulp (such as bleached kraft softwood or hardwood), flax, hemp, peat moss, abaca, bamboo, eucalyptus, bagasse, milkweed fluff, wheat straw, kenaf, and rayon.

In an illustration of one embodiment, "fiber" refers to cellulosic fibers commonly known as wood pulp fibers. Applicable wood pulps include chemical pulps, such as Kraft, sulfite, soda, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. U.S. Pat. No. 4,300,981 and U.S. Pat. No. 3,994,771 are incorporated herein by reference for the purpose of disclosing layering of hardwood and softwood fibers. Also applicable to an embodiment are fibers derived from recycled paper, which may contain any or all of the above categories as well as other non-fibrous materials such as fillers and adhesives used to facilitate the original papermaking.

In addition to the various wood pulp fibers, other cellulosic fibers such as cotton linters, rayon, lyocell, and bagasse can be used in an embodiment. Other sources of cellulose in the form of fibers or capable of being spun into fibers include grasses and grain sources.

"Pulp sheet" as used herein means a composite of individual pulp fibers that have been arranged together as a result of a pulping process. In one example, as is known by those of ordinary skill in the art, a bale of pulp comprises multiple individual pulp sheets in a stack. A pulping process is any process by which plant material (wood, grass, straw etc.) is reduced to a fibrous mass. It is achieved by rupturing bonds within plant structures. It can be accomplished mechanically, thermally, chemically or some combinations of these treatments. For avoidance of doubt, clearly low density (for example less than 0.15 g/cm$^3$) fibrous structures, such as fibrous structures produced by a papermaking process (individual plies thereof or finished products) used in bath tissue, paper towels, and/or facial tissue, are not considered pulp sheets for purposes of the present invention.

"Attach" and/or "attaching" as used herein means connecting (for example, joining, linking and/or fastening together) two or more materials, such as two or more individual pulp sheets together. Further, attach and/or attaching means connecting by more than surface frictional engagement due to normal forces experienced between adjacent surfaces of two materials disposed in overlapping relation. In one example, the attached two or more individual pulp sheets are connected together such that separation of the individual pulp sheets from one another by forces applied by a defiberizer upon the connected individual pulp sheets is prevented. In one example, two or more individual pulp sheets that are attached to one another resist separating from one another when the forces applied by a defiberizer in the machine direction are greater than about 0.1 kgf (kilogram force) and/or greater than about 0.5 kgf and/or greater than about 1 kgf and/or greater than about 2 kgf and/or greater than about 5 kgf and/or greater than about 10 kgf.

"Machine Direction" or "MD" as used herein means the direction parallel to the flow of the pulp sheet into the defiberizer. The machine direction is typically parallel to the movement of any transfer device that transfers and/or transports a pulp sheet and/or strip of pulp to a defiberizer. More specifically, the MD means the direction in which an individual sheet of pulp is transferred from a stack of pulp sheets to an inlet of a defiberizer. In one example, one or more pulp sheets enter the inlet of the defiberizer in the machine direction of the defiberizer.

"Cross Machine Direction" or "CD" as used herein means the direction perpendicular to the MD.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Process for Making Absorbent Component

Referring to FIGS. 1-4, a process may comprise using an apparatus 10 configured for defiberizing pulp from a stack of pulp sheets 24, and forming an absorbent component 70, for example an air-laid absorbent component 70, by depositing the defiberized pulp onto a forming surface 28, which for example may be a fabric or patterned belt. The stack of pulp sheets 24 may be made up of a plurality of individual pulp sheets 14, wherein an individual pulp sheet 14 may have a thickness, t, of greater than 0.1 mm and/or greater than 0.5 mm and/or greater than 1 mm and/or greater than 2 mm and/or to about 20 mm and/or to about 15 mm and/or to about 10 mm and/or to about 6 mm In one embodiment, an individual pulp sheet 14 has a thickness in the range of about 3 mm to about 4 mm, including all 0.1 mm increments within the recited range, as shown in FIG. 3. An individual pulp sheet 14 can also have a thickness in the range of about 0.5 mm to about 5 mm, a width in the range of about 250 mm to about 1200 mm, and a height in the range of about 500 mm to about 1000 mm The stack of pulp sheets 24 may be positioned in proximity of a destacker 12. The individual pulp sheets 14 may be stacked in vertical, horizontal, or angled arrangement to one another, as shown in FIGS. 2A-2C respectively. The destacker 12 acts on one or more individual pulp sheets 14. The destacker 12 may comprise, for example, a suctioning device, clamping device, or other suitable device that removes one or more individual pulp sheets 14 from the stack of pulp sheets 24. The destacker 12 may then deposit the individual pulp sheet 14 on a transfer device 34, such as a conveyor, carrier, belt, or other device suitable for transferring an individual pulp sheet 14 up to or through a series of processes. In one embodiment, a motor may mechanically drive the transfer device 34. For example, the transfer device 34 may be a conveyor, as is known in the art, having two generally parallel sides, which are typically parallel to the MD and a generally flat planar surface 35 on which the individual pulp sheets may be deposited and moved along the MD toward a defiberizer 22. For example, an individual pulp sheet 14 may be positioned so that a first face 36 of the individual pulp sheet 14, as shown in FIG. 3, lays substantially flat on a generally flat planar surface 35 of the transfer device 34 as shown in FIG. 1; that is, a plane of the first face 36 of an individual pulp sheet 14 may be positioned substantially parallel to a plane of the surface of the transfer device 34. In an additional embodiment, for example, the individual pulp sheet 14 may be positioned, at least at some time prior to entering the defiberizer 22, so that the first face 36 is substantially perpendicular to or in angled relation to the generally flat planar surface 35 of the transfer device 34.

In one embodiment, as shown in FIG. 1, a subsequent individual pulp sheet 14 may be removed from the stack of pulp sheets 24 by the destacker 12 and deposited on the transfer device 34. This subsequent individual pulp sheet 14, referred to as a second individual pulp sheet 48, may be placed on the transfer device 34 in contact (such as in an overlapping relationship and/or an abutting relationship) with a first individual pulp sheet 46 already present on the transfer device 34. The first individual pulp sheet 46 and second individual pulp sheet 48 may be in contact with each other and/or subsequent and/or preceding individual pulp sheets 14 in a variety of ways, each of which facilitates attachment of two or more individual pulp sheets 14, for example, the first individual pulp sheet 46 and the second individual pulp sheet 48. Further to the above, for example, a second individual pulp sheet 48 may be positioned such that there exists an overlap portion 40 between a face 36 or 42 of a first individual pulp sheet 46 and a face 36 or 42 of a second individual pulp sheet 48, as shown in FIGS. 1, 4A-4C, 5A-5C, and 6. In an additional example embodiment, as shown in FIGS. 1 and 7, a first individual pulp sheet 46 and a second individual pulp sheet 48 may be positioned in contact with one another such that at least one edge 38 of the first individual pulp sheet 46 and at least one edge 38 of the second individual pulp sheet 48 are in contact with one another resulting in an abutted portion 44 between the adjacent pulp sheets. The overlap portion 40 and/or abutted portion 44 may be created by the rate at which the destacker 12 deposits the individual pulp sheets 14 and/or by the use of other mechanical devices such as a photo eye or trigger device as is known to those of ordinary skill in the art. In addition, the overlap portion 40 and/or abutted portion 44 may be the result of manually positioning the first individual pulp sheet 46 and the second individual pulp sheet 48 on a surface of a transfer device 34.

In one embodiment, as shown in FIG. 1, a first individual pulp sheet 46 and a second individual pulp sheet 48 are positioned on the transfer device 34 in contact with at least a portion of one another. A first individual pulp sheet 46 and a second individual pulp sheet 48 each have the structural characteristics of an individual pulp sheet 14 as shown in FIG. 3. Thus, the first individual pulp sheet 46 and the second individual pulp sheet 48 both comprise at least one edge 38. In one embodiment, at least one edge 38 of a first individual pulp sheet 46 and/or at least one edge 38 of a second individual pulp sheet 48 may be substantially parallel to the MD and/or the movement of the transfer device 34, and at least one additional edge 38 of a first individual pulp sheet 46 and/or at least one additional edge 38 of the second individual pulp sheet 48 may be substantially perpendicular to the MD and/or the movement of the transfer device 34. Examples of various orientations of the first individual pulp sheet 46 and the second individual pulp sheet 48 will be addressed in more detail below.

In one embodiment, the transfer device 34 may move the first individual pulp sheet 46 and the second individual pulp sheet 48 so that the overlap portion 40 and/or abutted portion 44 pass through an attaching operation comprising, for example an attaching mechanism 16 capable of attaching the first individual pulp sheet 46 to one or more second individual pulp sheets 48. Non-limiting examples of attaching operations comprise subjecting the overlap portion 40 and/or abutted portion 44 to a crimping, needle-punching, sewing, and/or embossing operation. The attaching operation may include mechanically attaching adjacent individual pulp sheets and/or adhering adjacent individual pulp sheets together. Non-limiting examples of a mechanical attachment, which will be addressed in more detail below, may comprise sewing, dovetailing, mechanically entangling, and interleaving.

As shown in the FIG. 1, in one embodiment, a first individual pulp sheet 46 may be attached to one or more second individual pulp sheets 48 to form a strip of pulp 18. The strip of pulp 18 is fed into a defiberizer 22 that exerts a force, parallel to the MD, on the strip of pulp 18. The strength of the attachment between individual pulp sheets 14, or, more specifically, a first individual pulp sheet 46 and one or more second individual pulp sheets 48, which make up the strip of pulp 18, can withstand a force greater than about 0.1 kgf (kilogram force) and/or greater than about 0.5 kgf and/or greater than about 1 kgf and/or greater than about 2 kgf and/or greater than about 5 kgf and/or greater than about 10 kgf.

In one embodiment, for example, the apparatus 10 shown in FIG. 1 may comprise a sheet feeder 20, which may be used to facilitate the movement of a strip of pulp 18 from a transfer device 34 into a defiberizer 22. In addition to the transfer device 34, the strip of pulp 18 may be fed by a series of drive rollers, or other equivalent drive mechanism (not shown), into a sheet feeder 20. The drive rollers (not shown) may interact with the strip of pulp 18 on the side opposite the transfer device 34 to ensure the strip of pulp 18 enters the sheet feeder 20 in the desired configuration. The sheet feeder 20 may comprise one or more rollers 21 that contact and drive the strip of pulp 18 along the MD toward the defiberizer 22.

In one embodiment, as shown in FIG. 1, the apparatus 10 comprises a defiberizer 22, such as a hammermill, disk mill, or other apparatus for separating fibers to form defiberized fibers 26 from an individual pulp sheet 14 and/or a strip of pulp 18. A non-limiting example of a suitable defiberizer 22 is a hammermill. An example of a suitable hammermill is commercially available from Oerlikon Neumag and Dan-Web.

In one embodiment, a strip of pulp 18 as shown in FIG. 4A, for example, allows pulp to be continually fed into an inlet 32 of a defiberizer 22. The constant feed of pulp allows the defiberizer 22 to produce a continuous flow of defiberized fibers 26 that may be subsequently discharged in a stream of air passing through an outlet 30 of the defiberizer 22. The defiberized fibers 26 are then deposited onto a forming surface 28 to form an absorbent component 70. The deposition of the defiberized fibers 26 onto the forming surface 28 may be aided by a vacuum device (not shown) located under the forming surface 28.

The resulting absorbent component 70, such as an absorbent core material, can have a basis weight of from about 50 to about 1000 grams per square meter, preferably from about 60 to about 800 grams per square meter, and more preferably from about 70 to about 700 grams per square meter.

The resulting absorbent component 70 can then be incorporated into an absorbent article (not shown), such as a diaper or feminine hygiene article, including adult incontinence products and catamenial products such as tampons, sanitary napkins, pantiliners, interlabial products, and the like. In one aspect, the present invention further relates to an absorbent article comprising a topsheet, a backsheet, and an absorbent component therebetween, the absorbent component being made according to the process of the present invention.

The process according to the present disclosure is preferably a continuous process. Such a continuous process is typically carried out at a relatively high rate of speed. The continuous process can be conducted at a speed of at least about 2 meters of fibrous material per minute, preferably at least about 10 meters of fibrous material per minute, and more preferably at least about 20 meters of fibrous material per minute.

The process of the present disclosure further encompasses a process wherein more than one outlet is utilized to form the absorbent component, such as two or three separate outlets.

The process of the present disclosure further encompasses a process wherein more than one defiberizer is utilized to provide defiberized fibers to an individual outlet, such as two, three or four defiberizers per outlet.

The process for making an absorbent component according to the present disclosure is preferably an air-laid process.

Strip of Pulp

A strip of pulp 18 may be configured in numerous ways. The following discusses various example embodiments for a strip of pulp 18. As discussed above, the individual pulp sheets 14 that create a strip of pulp 18 may be attached by an adhesive or mechanical attachment. A strip of pulp 18 may vary in thickness along its dimensions or it may be of relatively uniform thickness across its dimensions depending on the desired configuration of the individual pulp sheets 14. A variation in thickness of a strip of pulp 18 may result in a defiberizer 22 producing a variable volume of defiberized fibers 26, but the defiberizer 22 can still produce a substantially continuous flow of defiberized fibers 26 thereby avoiding any interruptions in the substantially continuous flow of defiberized fibers 26 exiting the defiberizer 22 via the outlet 30. In addition, in one embodiment, the width of the strip of pulp 18 in the CD should not exceed the width in the CD of the inlet 32 of the defiberizer 22.

Figure 4B:
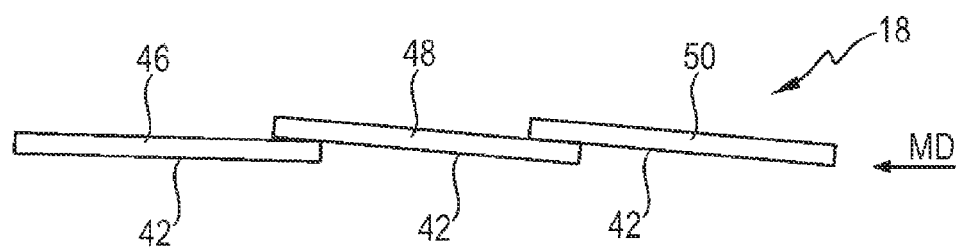
FIG. 4B is a side view of the strip of pulp of FIG. 4A.
Figure 4C:
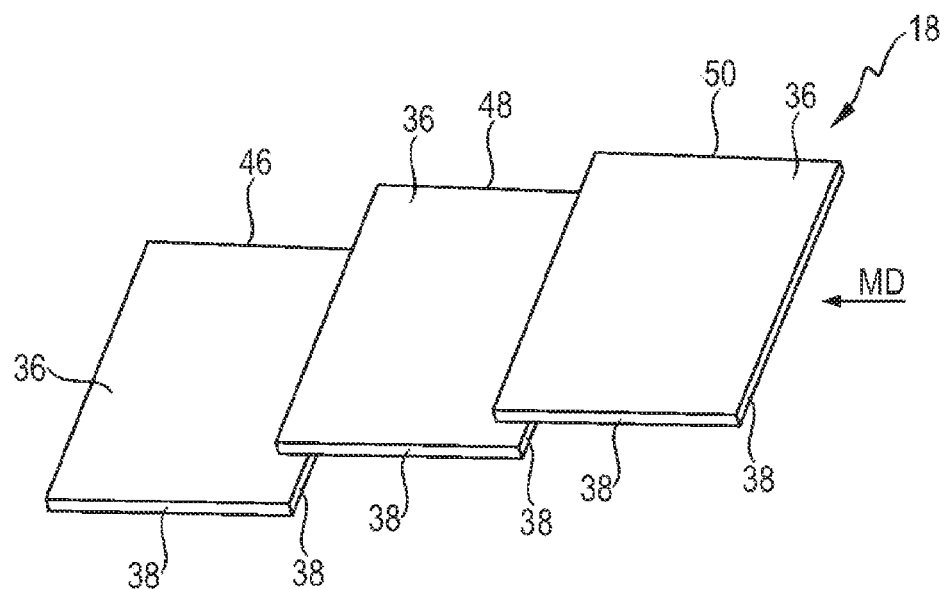
FIG. 4C is a perspective representation of another example embodiment of the strip of pulp of FIG. 4A.

In one embodiment, referring to FIGS. 4A-4C, a strip of pulp 18 may be assembled from one or more individual pulp sheets 14. A strip of pulp 18 may be assembled such that at least a portion of a second individual pulp sheet 48 is positioned on at least a portion of a first individual pulp sheet 46, and at least a portion of a third individual pulp sheet 50 is positioned on at least a portion of the second individual pulp sheet 48. More specifically, at least a portion of the second face 42 of the second individual pulp sheet 48 may overlap and be attached to at least a portion of the first face 36 of the first individual pulp sheet 46, and at least a portion of the second face 42 of the third individual pulp sheet 50 may overlap and be attached to at least a portion of the first face 36 of the second individual pulp sheet 48, as shown in FIGS. 4B and 4C. In one embodiment, a face 36 or 42 of one individual pulp sheet 14 overlaps less than 80% and/or less than 50% and/or less than 30% and/or less than 20% and/or less than 10% and/or less than 5% and/or less than 1% and/or 0% of the surface area of a face 36 or 42 of another individual pulp sheet 14. In another embodiment, adjacent first and second individual pulp sheets 46 and 48, respectively, have an overlap portion 40 that facilitates the attachment of the first individual pulp sheet 46 with the second individual pulp sheet 48. An overlap portion 40 is not necessary to attach individual sheets of pulp but is rather one example embodiment.

In one embodiment, as shown in FIG. 4C, adjacent individual pulp sheets 14 may be positioned such that at least one edge 38 of a first individual pulp sheet 46 and at least one edge 38 of a second individual pulp sheet 48 are in staggered relation to one another. Stated another way, at least one edge 38 of the first individual pulp sheet 46 may be substantially parallel to both the MD and at least one edge 38 of the second individual pulp sheet 48, and at least one edge 38 of the first individual pulp sheet 46 and at least one edge 38 of the second individual pulp sheet 48 are not coplanar. The plane of an edge 38 of the first individual pulp sheet 46 and the second individual pulp sheet 48 may be substantially perpendicular to an edge 38 of the first individual pulp sheet 46 and the second individual pulp sheet, respectively.

Figure 5A:
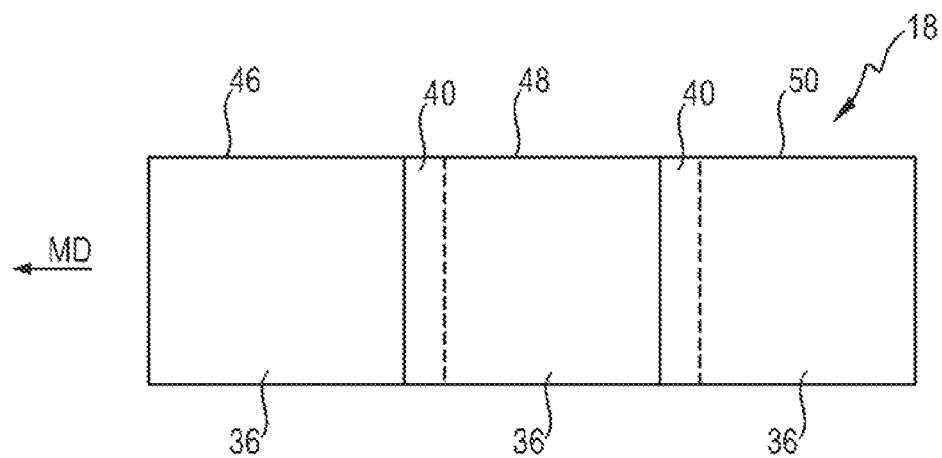
FIG. 5A is a schematic, top view of another example embodiment of a strip of pulp.
Figure 5B:
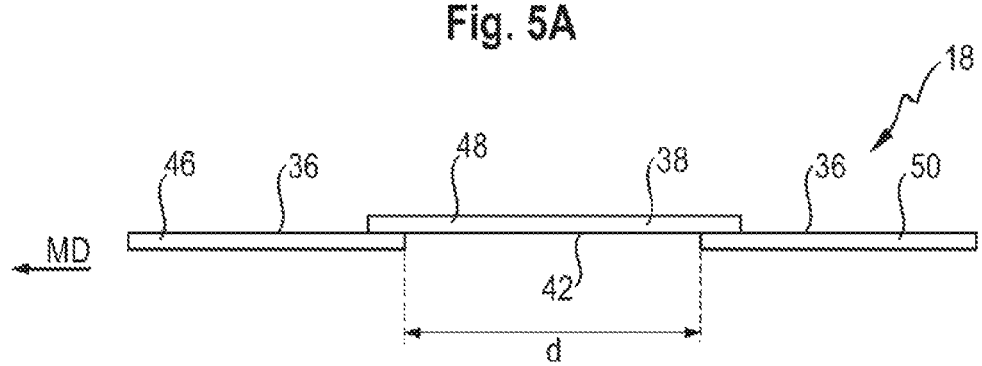
FIG. 5B is a side view of the strip of pulp of FIG. 5A.
Figure 5C:
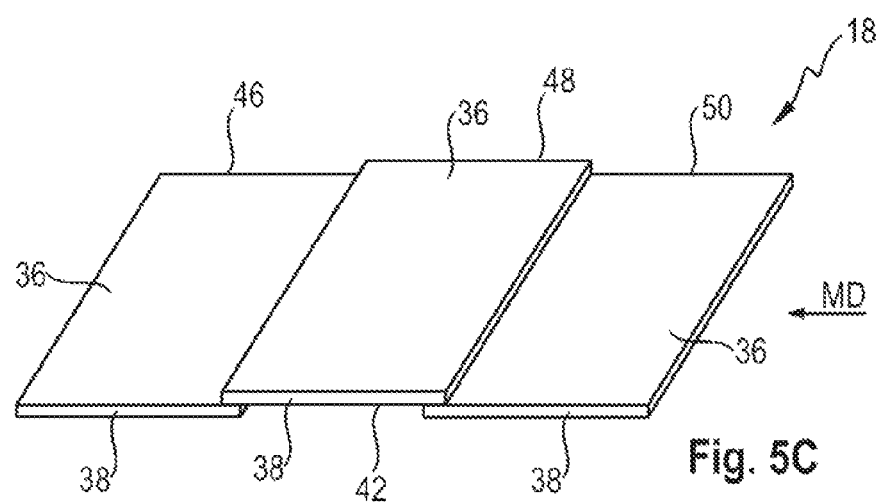
FIG. 5C is a perspective representation of the strip of pulp of FIG. 5A.

In one embodiment, referring to FIGS. 5A-5C, a strip of pulp 18 may be assembled by attaching one or more individual pulp sheets 14 such that a second individual pulp sheet 48 is positioned on at least a portion of both a first individual pulp sheet 46 and a third individual pulp sheet 50. More specifically, at least a portion of the second face 42 of the second individual pulp sheet 48 may be attached to at least a portion of the first face 36 of at least one of the first individual pulp sheet 46 and a third individual pulp sheet 50, as shown in FIGS. 5B and 5C. Referring to FIG. 5B, in one example embodiment, a first individual pulp sheet 46 may be separated by a distance, d, from a third individual pulp sheet 50. The distance, d, may be less than or equal to the length of the longest at least one edge 38 of the second individual pulp sheet 48. If, for example, in one embodiment the distance, d, was zero, the first individual pulp sheet 46 would abut the third individual pulp sheet 50. If, for example, in one embodiment, the distance, d, was equal to the length of at least one edge 38 of the second individual pulp sheet 48, least one edge 38 of the first individual pulp sheet 46 would abut at least one edge 38 of the second individual pulp sheet 48 and least one edge 38 of the third individual pulp sheet 50 would abut another at least one edge 38 of the second individual pulp sheet 48. In various embodiments, the distance, d, may be any distance less than or equal to the length of the longest edge 38 of an individual sheet of pulp in any 0.1 inch increment. In addition, in one embodiment, the overlap portion 40 may be equivalent to the length of at least one edge 38 subtracted from the distance, d, between the first individual pulp sheet 46 and the third individual pulp sheet 50. The overlap portion 40 may be a single overlap portion 40 or multiple overlap portions 40. If there is more than a single overlap portion 40, the overlap portion 40 created by the first individual pulp sheet 46 and the second individual pulp sheet 48 may be equal to or unequal to the overlap portion 40 created by the second individual pulp sheet 48 and the third individual pulp sheet 50.

Figure 6:
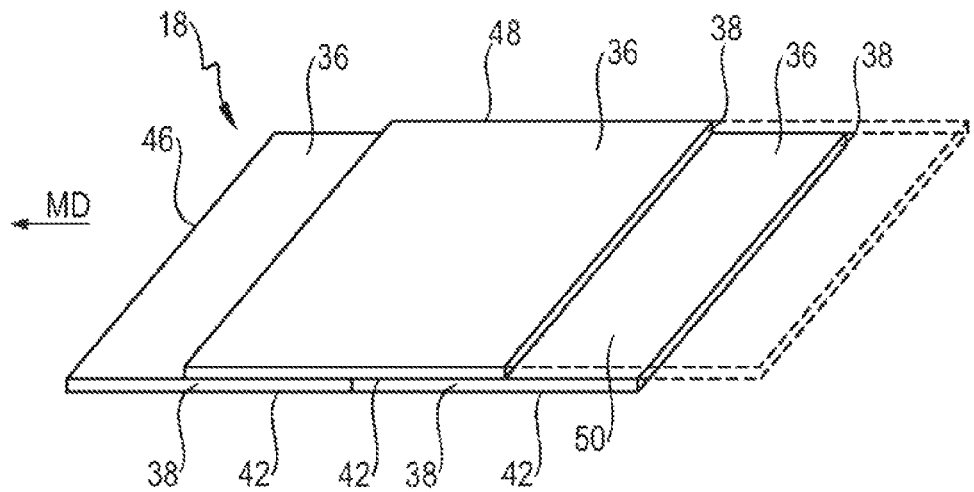
FIG. 6 is a schematic, perspective representation of another example embodiment of a strip of pulp.
Figure 7:
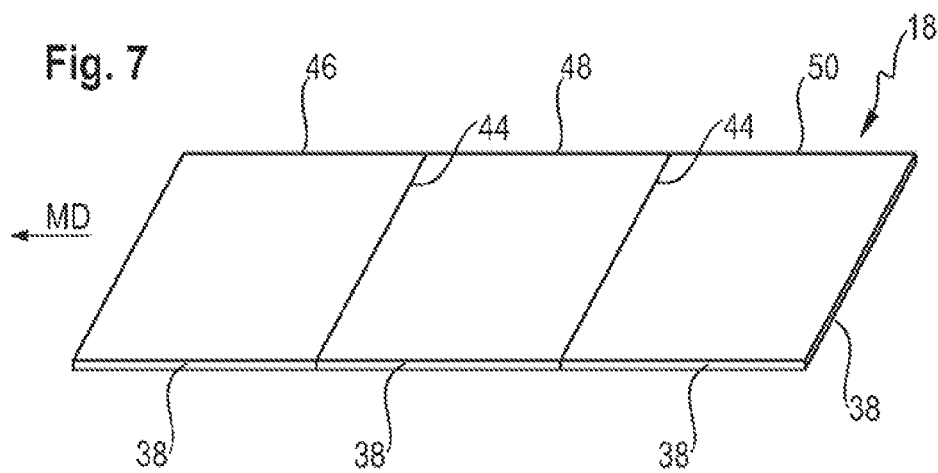
FIG. 7 is a schematic, perspective representation of another example embodiment of a strip of pulp.

In one embodiment, referring to FIG. 6, a strip of pulp 18 may be assembled from two or more individual pulp sheets 14 such that the strip of pulp 18 may have a relatively uniform thickness of two or more individual pulp sheets 14. The strip of pulp 18 may be assembled such that a first individual pulp sheet 46 is placed in contiguous relation to or abuts and attaches to a third individual pulp sheet 50, and the second face 42 of the second individual pulp sheet 48 overlaps and attaches to at least a portion of the first face 36 of at least one of the first individual pulp sheet 46 and the third individual pulp sheet 50. More specifically, at least a portion of the second face 42 of the second individual pulp sheet 48 may be placed on at least a portion of the first face 36 of the first individual pulp sheet 46 and the third individual pulp sheet 50, and at least a portion of at least one edge 38 of the first individual pulp sheet 46 abuts at least a portion of at least one edge 38 of a third individual pulp sheet 50. Individual pulp sheets 14 adjacent to the strip of pulp 18 configuration, as described above, may abut at least a portion of at least one edge 38 of the second individual pulp sheet 48 and/or the third individual pulp sheet 50. In an alternate embodiment, the strip of pulp 18 may be formed such that individual pulp sheets 14 adjacent to the strip of pulp 18 configuration, as previously disclosed, are spaced some distance, d, apart such that at least one edge 38 of the second individual pulp sheet 48 is not interacted with by an adjacent individual pulp sheet 14 and/or at least one edge 38 of the third individual sheet 50 is not interacted with by an adjacent individual pulp sheet 14.

In one embodiment, referring to FIG. 7, a strip of pulp 18 of relatively uniform thickness may be assembled from two or more individual pulp sheets 14. The strip of pulp 18 may be assembled such that at least one edge 38 of a first individual pulp sheet 46 abuts and attaches to at least a portion of at least one edge 38 of a second individual pulp sheet 48 to form an abutted portion 44, and at least one edge 38 of a second individual pulp sheet 48 abuts and attaches to at least a portion of at least one edge 38 of a third individual pulp sheet 50 to form an abutted portion 44. In one embodiment, at least one edge 38 of a first individual pulp sheet 46 may be substantially planar to at least one edge 38 of a second individual pulp sheet 48 and at least one edge 38 of a third individual pulp sheet 50.

Figure 8:
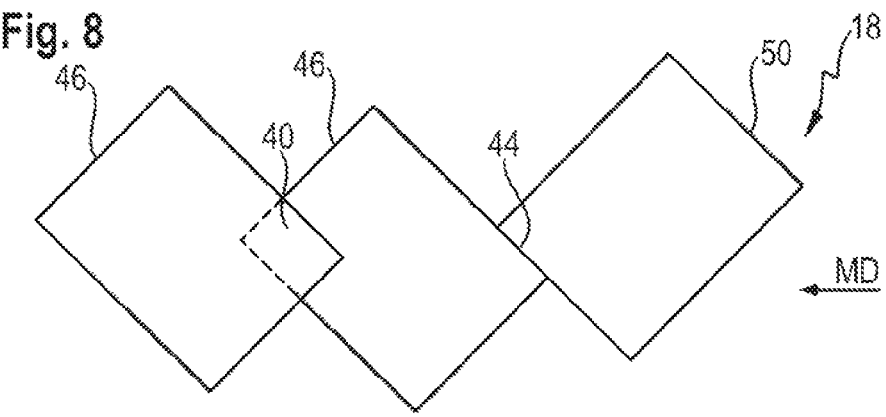
FIG. 8 is a schematic, top view of another example embodiment of a strip of pulp.

In one embodiment, referring to FIG. 8, a strip of pulp 18 may be configured such that the individual sheets of pulp 18 are attached in angled relation to one another. In one example embodiment, a strip of pulp 18 may be assembled such that at least one edge 38 of a first individual pulp sheet 46 and/or a second individual pulp sheet 48 and/or a third individual pulp sheet 50 is placed at an angle to the MD. More specifically, at least one edge 38 of a first individual pulp sheet 46 and/or a second individual pulp sheet 48 and/or a third individual pulp sheet 50 forms an angle of greater than about 5 degrees and/or greater than about 15 degrees and/or greater than about 30 degrees and/or greater than about 45 degrees and/or greater than about 60 degrees and/or greater than about 75 degrees and/or equal to about 90 degrees. In another example embodiment, a second individual pulp sheet 48 may abut or overlap at least a portion of first individual pulp sheet 46 and a third individual pulp sheet 50. More specifically, a first individual pulp sheet 46 may form an overlap portion 40 with a second individual pulp sheet 48, and a second individual pulp sheet 48 may form an abutted portion 44 with a third individual pulp sheet 50.

In one embodiment, referring to FIGS. 9 and 10, adjacent individual pulp sheets 14 may be configured such that at least a portion of each individual pulp sheet 14 is in contact with another individual pulp sheet 14. As shown in FIG. 9, for example, at least a portion of at least one edge 38 of a first individual pulp sheet 46 may abut and attach to at least a portion of at least one edge 38 of a second individual pulp sheet 48. In another embodiment, a first individual pulp sheet 46 may overlap and attach to at least a portion of a second individual pulp sheet 48. In an alternate, example embodiment, a third individual pulp sheet 50 may abut and attach to at least one edge 38 of the first individual pulp sheet 46 and/or at least one edge 38 of the second individual pulp sheet 48. In still another example embodiment, a third individual pulp sheet 50 may overlap and attach to at least a portion of the first individual pulp sheet 46 and/or the second individual pulp sheet 48.

As shown in FIG. 10, individual pulp sheets 14 having two or more edges 38 that may not be of equal length may be assembled to form a strip of pulp 18. For example, a first individual pulp sheet 46 may be positioned such that one or more of its longer edges 38 contacts at least a portion of a second individual pulp sheet's 48 one or more shorter edges 38 and vice versa. Depending on the length of the longer edge 38 of the first individual pulp sheet 46, one or more second individual pulp sheets 48 may abut the longer edge 38 of the first individual pulp sheet 46. In another example embodiment, one or more of the second individual pulp sheets 48 may overlap the first individual pulp sheet 46.

In one embodiment, referring to FIGS. 11 and 12, two or more strips of pulp 18 may be combined together to form a combined strip of pulp 56. For example, a combined strip of pulp 56 comprising a first strip of pulp 18 and one or more second strips of pulp 54, which may be attached to one another, may be fed into a defiberizer 22.

In one embodiment, one or more strips of pulp 18 may be assembled on different process lines and subsequently transferred to a common transfer device 34. For example, a first individual pulp sheet 46 may be attached to one or more second individual pulp sheets 48 to form a strip of pulp 18. In addition, a third individual pulp sheet 50 may be attached to one or more fourth individual pulp sheets 52 to form one or more second strips of pulp 54. The strip of pulp 18 and the one or more second strips of pulp 54 may be formed independently of one another and transferred to a common position, such as on a transfer device 34. The strip of pulp 18 may be positioned on at least a portion of one or more second strips of pulp 54 to form a combined strip of pulp 56. In one embodiment, the strip of pulp 18 may not be attached to one or more second strips of pulp 54 to form the combined strip of pulp 56. In another embodiment, the strip of pulp 18 may be attached to one or more second strips of pulp 54 to form the combined strip of pulp 56. In another example embodiment, the combined strip of pulp 56 may be formed such that at least one edge 38 of the strip of pulp 18 is substantially parallel to both the MD and at least one edge 38 of one or more second strips of pulp 54. In an example embodiment, the combined strip of pulp 56 may be formed such that at least one edge 38 of the strip of pulp 18 is substantially planar to at least one edge 38 of one or more second strips of pulp 54. In various embodiments, the combined strip of pulp 56 may have a thickness greater than two individual pulp sheets 14. The strip of pulp 18 and one or more second strips of pulp 54 may be formed in any of the previously discussed configurations and any additional configuration that would be known to one of ordinary skill in the art.

The attaching operation may include mechanically attaching adjacent individual pulp sheets and/or adhering adjacent individual pulp sheets together. Non-limiting examples of a mechanical attachment may comprise sewing, dovetailing, mechanically entangling, and/or interleaving.

In one embodiment, mechanically attaching comprises sewing. Sewing a first individual pulp sheet 46 to one or more second individual pulp sheets 48 may involve additional material such as a piece of thread. Such additional material may be present throughout a defiberizing process and ultimately in a product. In one embodiment, the additional material used for attaching the sheets of pulp is of a structure and/or characteristic so as to avoid creating clumping issues in the defiberizer 22 and/or discrepancies and/or defects in a product, such as a absorbent component, incorporating the defiberized fibers 26. Clumping, generally, refers to a dense group or groups of fibers that become entangled in the defiberizer 22. Clumping is generally undesirable for paper products, such as facial tissue, paper towels, and bath tissue, because clumps may lead to inconsistencies in properties and/or visible variations in a product, such as a absorbent component, incorporating the defiberized fibers 26. In addition, the additional material should minimize changes in the quality or characteristics of the product. In one embodiment, the additional material used to attach the individual pulp sheets 14 may comprise, for example, a dissolvable thread or a fibrous thread as commonly used in industrial sewing applications, such as nylon, polypropylene and/or cellulose, for example cotton.

Figure 13:
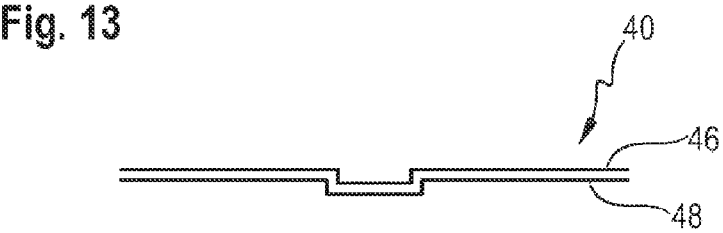
FIG. 13 is a schematic, side view of an example embodiment of a mechanically entangled strip of pulp.
Figure 14:
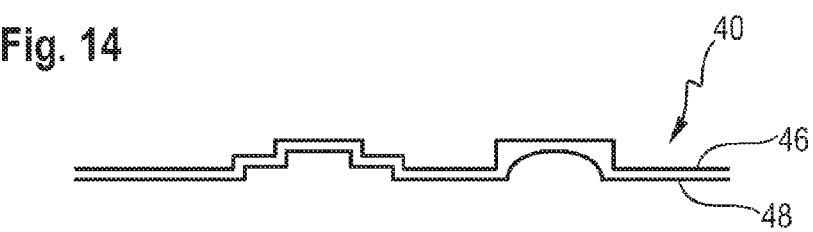
FIG. 14 is a schematic, side view of another example embodiment of a mechanically entangled strip of pulp.

In one embodiment, the individual pulp sheets 14 may be attached by mechanically entangling as shown in FIGS. 13 and 14. In one embodiment, a first individual pulp sheet 46 overlaps at least a portion of one or more second individual pulp sheets 48, and the overlap portion 40 may be mechanically entangled to attach a first individual pulp sheet 46 to one or more second individual pulp sheets 48. In one embodiment, mechanically entangling may comprise deforming at least a portion of or a localized area of the first individual pulp sheet 46. One or more second individual pulp sheets 48 may be deformed, either concurrently or subsequent to the first individual pulp sheet 46, to substantially match the deformation of the first individual pulp sheet 46 such that the first individual pulp sheet 46 fits within the one or more second individual pulp sheets 48. The localized deformations in at least one of the first face 36 and the second face 42 of the first individual pulp sheet 46 and one or more second individual pulp sheets 48 may be used to attach the first individual pulp sheet 46 to the one or more second individual pulp sheets 48. In another embodiment, the one or more localized deformations in the first individual pulp sheet 46 and the one or more second individual pulp sheets 48 may be different, as shown in FIG. 14. The attachment of the first individual pulp sheet 46 to the one or more second individual pulp sheets 48 may withstand the force, which is parallel to the MD, the defiberizer 22 exerts on the first individual pulp sheet 46. Thus, the one or more second individual pulp sheets 48 remain attached to the first individual pulp sheet 46 as the strip of pulp 18 is fed into the defiberizer 22. The first individual pulp sheet 46 and the one or more second individual pulp sheets 48 may be mechanically entangled, for example, by feeding the overlap portion 40 through an embossing operation.

In one embodiment, attaching two or more individual pulp sheets 14 together by adhering can comprise gluing and/or taping a first individual pulp sheet 46 to one or more second individual pulp sheets 48. Analogous to the above with respect to mechanically attaching, the adhesive material (glue) may consist of a material which avoids creating clumping issues in the defiberizer 22 and/or discrepancies and/or defects in a product, such as a absorbent component, incorporating the defiberized fibers 26 for the same reasons described above. In addition, the adhesive material should minimize changes in the quality or characteristics of the product. Non-limiting examples of adhering may comprise taping and gluing. In one embodiment, two or more individual pulp sheets may be attached together by tape. A non-limiting example of a suitable tape is commercially available from 3M or Anchor Continental. In another embodiment, two or more individual pulp sheets 14 may be attached together by a glue, for example a water-based glue. Non-limiting examples of suitable glues are commercially available from H. B. Fuller under the trade names WB-4955M, WB-4989 and WB-4997, Henkel under the brand name Adhesin® and National Starch & Chemical Company.

Figure 15:
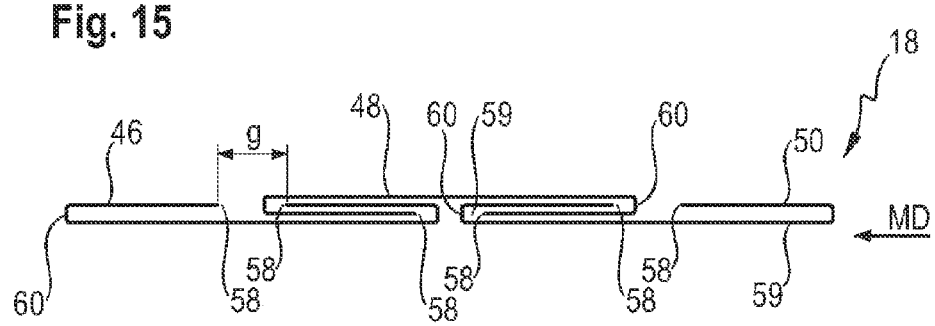
FIG. 15 is a schematic, side view of an example embodiment of an interleaved strip of pulp.

In one embodiment, the individual pulp sheets 14 may be attached by interleaving a first individual pulp sheet 46 with one or more second individual pulp sheets 48 and a third individual pulp sheet 50, as shown in FIG. 15. Each of a first individual pulp sheet 46, a second individual pulp sheet 48, and a third individual pulp sheet 50 may be placed in a C-shaped configuration and interleaved to prevent the separation along the MD of the first individual pulp sheet 46 from the second individual pulp sheet 48 and the third individual pulp sheet 50. The interleaving may be performed manually or by a machine. In one embodiment, to assemble the individual pulp sheets 14 in an interleaving configuration, a first individual pulp sheet 46 may be bent such that a cavity 59 is formed between the at least one end 58 and at least a portion of a face 36 or 42 of the first individual pulp sheet 46. Further, each end 58 may be separated from one another by a gap, g. The gap, g, may be large enough to accept at least a portion of at least one and/or two and/or more individual pulp sheets 14. A second individual pulp sheet 48 may be bent in a similar C-shaped configuration as the first individual pulp sheet 46. The second individual pulp sheet 48 may be rotated opposite the first individual pulp sheet 46. An end 58 of the second individual pulp sheet 48 may be inserted into the gap g of the first individual pulp sheet 46 such that the second individual pulp sheet 48 substantially surrounds at least a portion of one end 58 of the first individual pulp sheet 46. A third individual pulp sheet 50 may be bent in a similar C-shaped configuration as both the first individual pulp sheet 46 and the second individual pulp sheet 48. The second individual pulp sheet 48 substantially surrounds at least a portion of an end 58 of the third individual pulp sheet 50. The first individual pulp sheet 46 may be interleaved with the second individual pulp sheet 48 and the third individual pulp sheet 50 to form a strip of pulp 18. In one embodiment, the strip of pulp 18 may have a substantially uniform thickness. In another embodiment, the bend 60 and each end 58 of the first individual pulp sheet 46 may be substantially perpendicular to the MD. Thus, a defiberizer 22 may exert a force on the first individual pulp sheet 46 that is substantially perpendicular to the bend 60 of the first individual pulp sheet 46.

In one embodiment, two or more pulp sheets are attached to one another using a material that is acceptable for inclusion in a product into which the defiberized fibers 26 are ultimately incorporated.

In another embodiment, the attaching operation comprises a step of controlling the moisture level of the pulp sheets prior to and/or during and/or post the attaching operation. In one embodiment, the moisture level of the pulp sheets prior to and/or during the attaching operation is greater than 5% and/or greater than 6% and/or greater than 8% and/or greater than 10% by weight of the pulp sheet.

In another embodiment, the strip of pulp 18 may be assembled with multiple attachments. For example, the first individual pulp sheet 46 may be adhered to the one or more second individual pulp sheets 48, and the one or more second individual pulp sheets 48 may be mechanically attached to the third individual pulp sheet 50. More specifically, the first individual pulp sheet 46 may be glued to the one or more second individual pulp sheets 48, and the one or more second individual pulp sheets 48 may be sewn to the third individual pulp sheet 50. Any type of attachment as described above may be used in conjunction with other types of attachment to assemble a strip of pulp 18.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making an absorbent component, the process comprising the steps of:

providing individual sheets of pulp, each sheet of pulp having a face;
attaching a first individual pulp sheet to one or more second individual pulp sheets to form a strip of pulp, wherein the face of the first individual pulp sheet overlaps less than 30% of a surface area of the face of the second individual pulp sheet;
feeding the strip of pulp into a defiberizer;
defiberizing the strip of pulp to form defiberized fibers; and
depositing the defiberized fibers onto a forming surface to form the absorbent component.

2. The process for making an absorbent component of claim 1, wherein the process further comprises the step of positioning at least a portion of the first individual pulp sheet in contact with at least a portion of at least one of the one or more second individual pulp sheets.

3. The process for making an absorbent component of claim 2, wherein the step of positioning comprises abutting at least a portion of the first individual pulp sheet to at least a portion of at least one of the one or more second individual pulp sheets.

4. The process for making an absorbent component of claim 2, wherein the step of positioning comprises overlapping at least a portion of the first individual pulp sheet with at least a portion of at least one of the one or more second individual pulp sheets.

5. The process for making an absorbent component of claim 1, wherein the step of attaching comprises mechanically attaching the first individual pulp sheet to at least one of the one or more second individual pulp sheets.

6. The process for making an absorbent component of claim 5, wherein the step of mechanically attaching comprises sewing the first individual pulp sheet to at least one of the one or more second individual pulp sheets.

7. The process for making an absorbent component of claim 5, wherein the step of mechanically attaching comprises dovetailing the first individual pulp sheet to the one or more second individual pulp sheets.

8. The process for making an absorbent component of claim 5, wherein the step of mechanically attaching comprises mechanically entangling the first individual pulp sheet to at least one of the one or more second individual pulp sheets.

9. The process for making an absorbent component of claim 5, wherein the step of mechanically attaching comprises needle punching the first individual pulp sheet to the one or more second individual pulp sheets, wherein one or more fibers of the first individual pulp sheet are in contact with one or more fibers of the one or more second individual pulp sheets.

10. The process for making an absorbent component of claim 5, wherein the step of mechanically attaching comprises interleaving the first individual pulp sheet to at least one of the one or more second individual pulp sheets.

11. The process for making an absorbent component of claim 1, wherein the step of attaching comprises adhering the first individual pulp sheet to at least one of the one or more second individual pulp sheets.

12. The process for making an absorbent component of claim 11, wherein the step of adhering comprises taping the first individual pulp sheet to at least one of the one or more second individual pulp sheets.

13. The process for making an absorbent component of claim 11, wherein the step of adhering comprises gluing the first individual pulp sheet to at least one of the one or more second individual pulp sheets.

14. The process for making an absorbent component of claim 1, wherein the first individual pulp sheet comprises at least one edge, wherein the at least one edge is perpendicular to the machine direction of the defiberizer when feeding the strip of pulp into the defiberizer.

15. The process for making an absorbent component of claim 1, wherein the first individual pulp sheet comprises at least one edge, wherein the at least one edge is at an angle in the range of about 5 degrees to about 90 degrees to the machine direction of the defiberizer when feeding the strip of pulp into the defiberizer.

16. The process for making an absorbent component of claim 1, wherein the first individual pulp sheet comprises at least one edge, wherein the at least one edge is substantially parallel to the machine direction of the defiberizer when feeding the strip of pulp into the defiberizer.

17. The process for making an absorbent component of claim 1, wherein the thickness of the first individual pulp sheet is in the range of from about 0.5 mm to about 5 mm.

18. The process for making an absorbent component of claim 1, wherein the process further comprises the step of removing the first individual pulp sheet from a stack comprising a plurality of individual pulp sheets.

19. The process for making an absorbent component of claim 1, wherein the process further comprises the step of depositing the first individual pulp sheet on a transfer device, wherein the transfer device moves the first individual pulp sheet toward the defiberizer.

20. The process for making an absorbent component of claim 1, wherein the process further comprises the step of aligning the first individual pulp sheet on the transfer device, wherein the first individual pulp sheet comprises a first face and a second face, wherein the first face is substantially perpendicular to a plane of the transfer device.

* * * * *